(12) United States Patent
Javois et al.

(10) Patent No.: US 8,828,051 B2
(45) Date of Patent: Sep. 9, 2014

(54) LEFT ATRIAL APPENDAGE OCCLUSION DEVICE

(75) Inventors: Alex Javois, Hinsdale, IL (US); Franz Freudenthal, La Paz (BO)

(73) Assignee: PFM Medical AG, Cologne (DE)

(*) Notice: Subject to any disclaimer, the term of this patent is extended or adjusted under 35 U.S.C. 154(b) by 224 days.

(21) Appl. No.: 13/173,702

(22) Filed: Jun. 30, 2011

(65) Prior Publication Data

US 2012/0065667 A1 Mar. 15, 2012

Related U.S. Application Data

(60) Provisional application No. 61/361,097, filed on Jul. 2, 2010.

(51) Int. Cl.
*A61B 17/08* (2006.01)
*A61B 17/12* (2006.01)

(52) U.S. Cl.
CPC . *A61B 17/12122* (2013.01); *A61B 2017/12054* (2013.01); *A61B 17/12172* (2013.01)
USPC ...................................... 606/213

(58) Field of Classification Search
USPC .......... 606/213, 139, 151, 191, 200, 215, 216
See application file for complete search history.

(56) References Cited

U.S. PATENT DOCUMENTS

| | | |
|---|---|---|
| 5,649,949 A | 7/1997 | Wallace et al. |
| 5,725,552 A | 3/1998 | Kotula et al. |
| 5,846,261 A | 12/1998 | Kotula et al. |
| 5,911,734 A | 6/1999 | Tsugita et al. |
| 5,944,738 A | 8/1999 | Amplatz et al. |
| 6,010,517 A | 1/2000 | Baccaro |
| 6,024,765 A | 2/2000 | Wallace et al. |
| 6,033,423 A | 3/2000 | Ken et al. |
| 6,059,825 A | 5/2000 | Hobbs et al. |
| 6,080,182 A | 6/2000 | Shaw et al. |
| 6,117,157 A | 9/2000 | Tekulve et al. |
| 6,123,715 A | 9/2000 | Amplatz |
| 6,152,144 A | 11/2000 | Lesh et al. |
| 6,171,329 B1 | 1/2001 | Shaw et al. |

(Continued)

FOREIGN PATENT DOCUMENTS

WO WO 2008/125689 A1 10/2008

OTHER PUBLICATIONS

Al-Saady et al., "Left atrial appendage: structure; function, and role in thromboembolism," Heart, 82:547-554 (1999).

(Continued)

*Primary Examiner* — Gregory Anderson
(74) *Attorney, Agent, or Firm* — Foley & Lardner LLP (57) ABSTRACT

A left atrial appendage occlusion device including an occluder disk configured to substantially prevent blood from at least one of entering and exiting the left atrial appendage, a middle portion including a coiled element and a first anchoring element. The coiled element connects to the occluder disk, has a substantially constant cross section and allows for variable length, variable orientation, and/or varied angles. The first anchoring element connects to the coiled element and includes scalloped edges that are configured to anchor the occlusion device to inner walls of the left atrial appendage and reduce the risk of one of penetration and perforation of walls of the left atrial appendage. The left atrial appendage occlusion device may also include a self-centering element that connects to the occluder disk and middle portion and is configured to center the occlusion device within the orifice of the left atrial appendage.

18 Claims, 9 Drawing Sheets

(56) References Cited

U.S. PATENT DOCUMENTS

| | | |
|---|---|---|
| 6,206,907 B1 | 3/2001 | Marino et al. |
| 6,214,029 B1 | 4/2001 | Thill et al. |
| 6,338,736 B1 | 1/2002 | Boosfeld et al. |
| 6,368,339 B1 | 4/2002 | Amplatz |
| 6,375,671 B1 | 4/2002 | Kobayashi et al. |
| 6,463,317 B1 | 10/2002 | Kucharczyk et al. |
| 6,537,293 B1 | 3/2003 | Berryman et al. |
| 6,551,344 B2 | 4/2003 | Thill |
| 6,569,179 B2 | 5/2003 | Teoh et al. |
| 6,596,013 B2 | 7/2003 | Yang et al. |
| 6,652,555 B1 | 11/2003 | Van Tassel et al. |
| 6,723,108 B1 | 4/2004 | Jones et al. |
| 6,790,218 B2 | 9/2004 | Jayaraman |
| 7,288,105 B2 | 10/2007 | Oman et al. |
| 7,582,103 B2 | 9/2009 | Young et al. |
| 7,665,466 B2 | 2/2010 | Figulla et al. |
| 2002/0002382 A1 | 1/2002 | Wallace et al. |
| 2003/0195530 A1 | 10/2003 | Thill |
| 2004/0127935 A1 | 7/2004 | Van Tassel et al. |
| 2004/0158282 A1 | 8/2004 | Jones et al. |
| 2004/0186512 A1 | 9/2004 | Bruckheimer et al. |
| 2004/0243168 A1 | 12/2004 | Ferrera et al. |
| 2005/0004598 A1 | 1/2005 | White, Jr. et al. |
| 2005/0038460 A1 | 2/2005 | Jayaraman |
| 2005/0065546 A1 | 3/2005 | Corcoran et al. |
| 2005/0234543 A1 | 10/2005 | Glaser et al. |
| 2007/0034366 A1 | 2/2007 | Igami et al. |
| 2007/0043393 A1 | 2/2007 | Brockway et al. |
| 2007/0083230 A1 | 4/2007 | Javois |
| 2007/0106327 A1 | 5/2007 | Thill et al. |
| 2007/0112380 A1 | 5/2007 | Figulla et al. |
| 2007/0293890 A1 | 12/2007 | Corcoran et al. |
| 2008/0058866 A1 | 3/2008 | Young et al. |
| 2009/0012553 A1 | 1/2009 | Swain et al. |
| 2009/0112249 A1 | 4/2009 | Miles et al. |
| 2009/0234407 A1 | 9/2009 | Hastings et al. |
| 2010/0145361 A1 | 6/2010 | Francischelli et al. |
| 2010/0204716 A1 | 8/2010 | Stewart et al. |

OTHER PUBLICATIONS

Friedman et al., "Percutaneous Epicardial Left Atrial Appendage Closure: Preliminary Results of an Electrogram Guided Approach", Journal of Cardiovascular Electrophysiology, Apr. 2, 2009, 20(8):908-915 (advance publication pp. 1-8).

Sievert et al., "Precutaneous Left Atrial Appendage Transcatheter Occlusion to Prevent Stroke in Hihg-Risk Patients with Atrial Fibrillation," Circulation, 105:1887-1889 (2002).

LEFT ATRIAL APPENDAGE OCCLUSION DEVICE

CROSS-REFERENCE TO RELATED PATENT APPLICATIONS

This application claims priority to U.S. Provisional Application No. 61/361,097, filed Jul. 2, 2010, incorporated herein by reference in its entirety. This application is related to U.S. application Ser. No. 11/245,421, incorporated herein by reference in its entirety.

BACKGROUND

1. Field of Embodiments

The present embodiments relate generally to occlusion devices that are for use in the left atrial appendage ("LAA") or other suitable treatment sites.

2. Description of Related Art

The LAA is the small conical projection from the upper anterior portion of the left atrium. Blood pooling in the LAA may arise spontaneously or as a result of atrial fibrillation. When blood pools in the LAA, blood clots can form. The migration of clots from the LAA to the bloodstream can cause serious problems when the clots embolize in the arterial system. More than 90% of clots formed during atrial fibrillation are formed in the LAA. Sievert et al., CIRCULATION 105: 1887-1889 (2002). Embolization of these clots is a frequent cause of stroke. Thus, prevention of clot formation in, or clot migration from, the LAA may reduce the occurrences of stroke in patients with atrial fibrillation.

A common method of reducing the risk of clot formation is treatment with anticoagulants such as warfarin. Such treatment has been an effective method of reducing the incidence of stroke. However, strokes may still occur in patients using anticoagulants if there is a necessary or inadvertent lapse in treatment. Also, many patients who are at risk of stroke are contraindicated from using anticoagulants. Anticoagulant treatment is effective, but the difficulty in treating patients continuously and the high occurrence of contraindication give rise to a need for a different treatment option.

Another method of treatment designed to reduce clotting and embolization leading to stroke is LAA obliteration. Clearly, obliteration of the LAA will lead to less clotting during atrial fibrillation. Obliteration may occur during open cardiac surgery or via a less invasive thoracoscopic procedure. Many patients with a high risk of stroke are not candidates for such procedures because of their compromised health status. Further, obliteration of the LAA may have adverse haemodynamic and hormonal effects that have not been fully studied. See Al-Saady et al., HEART 82:547-554 (1999).

The limitations of anticoagulant treatment and surgical obliteration of the LAA give rise to the need for a less invasive method and device to aid in preventing migration of clots from the LAA into the bloodstream.

Various devices have been developed and used for LAA occlusion. One such device includes a Nitinol cage enclosed in an ePTFE membrane. The device is designed to be inserted entirely into the LAA and has multiple anchors for attachment to the interior wall of the LAA. Because the device is designed to be inserted entirely into the LAA, the device must be properly sized to ensure complete occlusion of the LAA. Improper measurement of the LAA may lead to increased implantation times or decreased effectiveness of the device if the wrong size is implanted.

Another device includes a wire cage partially covered by an ePTFE membrane. This device is also designed to be inserted entirely within the LAA and includes no anchors for attachment within the LAA. As above, improper measurement of this device may result in increased implantation times or decreased effectiveness. Also, the lack of an anchoring mechanism allows migration of the device, which may lead to more serious complications if the device migrates out of the LAA.

Thus, the shortcomings of the existing devices may lead to longer procedures, incomplete occlusion of the LAA or other serious complications triggered by migration of the device out of the LAA. Furthermore, existing devices are oversized, potentially causing stretching of the LAA. For example, existing devices may be larger than the LAA by 20-25%. Such stretching may lead to life threatening perforation, erosion, arrhythmia or compression of circumflex coronary artery. The circumflex coronary artery is in close proximity to the orifice of the LAA.

A need exists for an improved LAA occlusion device and method for LAA occlusion, including a LAA occlusion device and method for LAA occlusion that may addresses one or more of the above described disadvantages. For example, a need exists for a LAA occlusion device and method that ensures complete occlusion or substantially complete occlusion of the LAA to aid in the prevention of clot formation and clot migration from the LAA in order to reduce the risk of stroke in patients with atrial fibrillation. Additionally, a need exists for a LAA occlusion devices that is effectively anchored to the musculature of the LAA to prevent excessive movement of the device or migration of the device out of the LAA, with minimal intentional penetration of the LAA. A need also exists for a LAA occlusion device that will provide complete occlusion or substantially complete occlusion of the LAA independent of the physiology of the patient in order to reduce implantation times and reduce complications caused by an oversized device.

SUMMARY

One embodiment relates to a left atrial appendage occlusion device that comprises an occluder disk, a middle portion and a first anchoring element. The occluder disk is configured to substantially prevent blood from at least one of entering and exiting the left atrial appendage. The middle portion includes a coiled element. The coiled element connects to the occluder disk, has a substantially constant cross section and allows for variable length of the occlusion device. The first anchoring element connects to the coiled element and includes scalloped edges that are configured to anchor the occlusion device to inner walls of the left atrial appendage and reduce the risk of one of penetration and perforation of walls of the left atrial appendage.

The left atrial appendage occlusion device may also include a self-centering element that connects to the occluder disk and the middle portion and that is configured to center the occlusion device within the orifice of the left atrial appendage.

BRIEF DESCRIPTION OF THE DRAWINGS

These and other features, aspects and advantages of the disclosed embodiments will become apparent from the following description, appended claims and the accompanying exemplary embodiments shown in the drawings, which are briefly described below.

DETAILED DESCRIPTION

Devices and methods for occluding the LAA are described. The devices and methods may completely occlude the LAA by preventing any blood flow into the LAA from occurring or may substantially occlude the LAA by allowing only a minimal amount of blood flow in and out of the LAA. The devices may include an easily deployed/delivered wire structure of shape memory material sized to be appropriate for use in any subject in need thereof. The subject can be, for example, a mammal, such as a dog or human. The methods may include deploying/delivering the device within the LAA, securely anchoring the device, and ensuring that the opening of the LAA is eclipsed or "sealed" by the device, particularly an occluder disc thereof.

Referring to FIGS. 1-10, a left atrial appendage occlusion device 1, 100, 200 comprises an occluder disk 2, 102, 202, a middle portion 97, 197, 297 and a first anchoring element 6, 106, 206. Although the occlusion device 1, 100, 200 is generally discussed as being delivered into the LAA, the occlusion device may be delivered into other suitable treatment sites.

The occluder disk 2, 102, 202 may comprise one or more wires. The wire(s) may form a wire mesh. It is easier to manufacture the occluder disk 2, 102, 202 when the occluder disk 2, 102, 202 is only made of one wire. For example, when the occluder disk 2, 102, 202 is only made of one wire, welding of the occluder disk is unnecessary. Such welding may fail resulting in failure of a portion of or the entire occlusion device, which may lead to severe complications. Such complications may include embolization of a part or of all of the occlusion device and/or may include failure of the occlusion device to occlude all of the LAA.

The wire(s) of the occluder disk 2, 102, 202 may be made from any type of suitable shape memory material that will cause the wire to form a preferred relaxed state configuration when introduced into the LAA. The material is selected for its biocompatibility, including its anti-thrombogenic capacity, its shape-recovery capabilities and superelasticity. The wire(s) may comprise a metal or a metal alloy. The metal or metal alloy may be, for example, a memory alloy. A memory alloy may comprise nickel, titanium or any other suitable material. For example, the memory alloy may be Nitinol®, which is a nickel-titanium alloy, Elgiloy®, titanium, stainless steel, other suitable material or combinations thereof.

The occluder disk 2, 102, 202 may include a first fabric material 12, 112, 212 that facilitates tissue growth over the occlusion device. The first fabric material 12, 112, 212 may be any suitable shape that fits within or on the surface of the occluder disk 2, 102, 202. For example, the first fabric material 12, 112, 212 may be a sheet, a plurality of sheets, a membrane or a random shape that fills up at least a portion of the inside of the occluder disk 2, 102, 202. When the occluder disk 2, 102, 202 is in its expanded shape (i.e. after deployment or being delivered into the LAA), the first fabric material 12, 112, 212 may extend along an inside surface of the occluder disk 2, 102, 202 in a flagged manner such that the length and width of the first fabric material 12, 112, 212, may extend along the inside surface of the occluder disk 2, 102, 202 for any length and width sufficient to ensure that the opening of the LAA will be substantially or completely eclipsed by the first fabric material 12, 112, 212. Such an eclipse, allows effective sealing of the LAA by the occluder disk 2, 102, 202 and the first fabric material 12, 112, 212 so as to effectively prevent blood flow into the LAA and/or any clots that may form in the LAA from migrating out of the LAA and into the bloodstream. Thus, the sheet first fabric material 12, 112, 212 aids in the prevention of embolisms that would normally cause severe mental and physical disabilities or death. The length of the first fabric material 12, 112, 212 may be greater than the width of the first fabric material 12, 112, 212 when extended in this manner. The first fabric material 12, 112, 212 may be placed within the occluder disk 2, 102, 202 during or after formation of the occluder disk 2, 102, 202. Alternately, the first fabric material may also be placed on the outside surface of the occluder disk.

The first fabric material 12, 112, 212 may be any suitable material that promotes and/or facilitates tissue growth so that tissue of the subject can grow in and around the occluder disk 2, 102, 202. For example, the fabric material 12, 112, 212 may be any suitable polyester fibers, such as Dacron®. Alternatively, the first fabric material 12, 112, 212 may be made of a biodegradable and/or biocompatible material such as expanded polytetrafluoroethylene (ePTFE), Teflon®, felt, Gortex® (a PTFE material), silicone urethane, metal fibers, other polymers, such as polypropylene, or combinations thereof. The first fabric material 12, 112, 212 may be impermeable to fluid, such as blood or body fluid.

Figure 10:
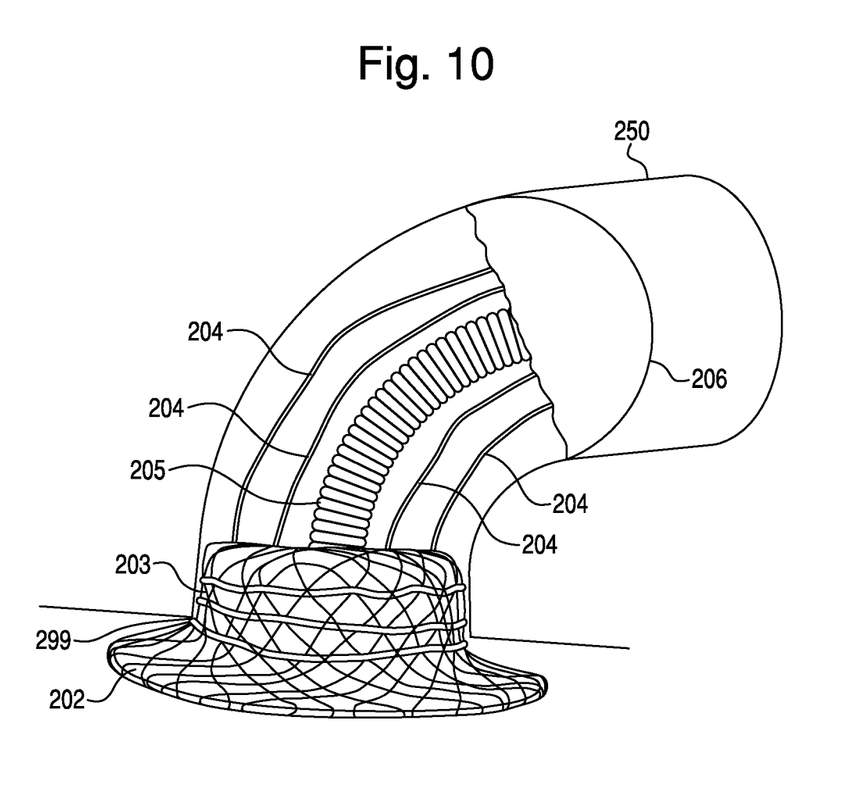
FIG. 10 is a side view of the occlusion device of FIG. 9 after being delivered into the LAA.

The occluder disk 2, 102, 202 is configured to substantially or completely prevent blood from entering and/or exiting the LAA 250 (FIG. 10). As shown in FIG. 10, when the occlusion device 1, 100, 200 is inserted into the LAA 250, the occluder disk 2, 102, 202 lies outside of the LAA and sides of the occluder disk 2, 102, 202 extend past the orifice 299 of the LAA 250 so that the enter orifice 299 of the LAA 250 is blocked by the occluder disk 2, 102, 202. Generally, the diameter of the occluder disk 2, 102, 202 is greater than the orifice 299 of the LAA 250. The positioning of the occluder disk 2, 102, 202 relative to the opening of the orifice 299 and the presence of the first fabric material 12, 112, 212 within or on the surface of the occluder disk 2, 102, 202 allows the occluder disk 2, 102, 202 to substantially or completely prevent blood from exiting the LAA 250.

The middle portion 97, 197, 297 is located between the occluder disk 2, 102, 202 and the first anchoring element 6, 106, 206 and includes a coiled element 5, 105, 205. The coiled element 5, 105, 205 connects to the occluder disk 2, 102, 202. The coiled element 5, 105, 205 allows for variable length of the occlusion device, which enables the occlusion device to account for varied shaped and dimensioned LAAs because no two LAAs are alike. The coiled element 5, 105, 205 also allows for varied angled and varied orientations of the occlusion device, which also enables the occlusion device to account for varied shaped and dimensioned LAAs because no two LAAs are alike. The coiled element 5, 105, 205 has a substantially constant or a constant cross section. Additionally, the coiled element 5, 105, 205 has substantially more coils per length of the coiled element than prior occlusion devices, such as the occlusion device in U.S. application Ser. No. 11/245,421. The coiled element 5, 105, 205 may be a spring or behave like a spring and may be shaped like a spring. The coiled element 5, 105, 205 may be made from inorganic material, such as stainless steel, and/or organic material, such as polymer coil. The coiled element 5, 105, 205 stretches to various lengths to accommodate the different lengths of the LAA in different subjects.

Once deployed/delivered into the LAA, the coiled element 5, 105, 205 may pull the occluder disk 2, 102, 202 toward the orifice 299 of the LAA 250 so that the sides of the occluder disk 2, 102, 102 abut and/or contact the sides of a subject next to the orifice 299 of the LAA 250 when the occlusion device 1, 100, 200 is deployed into the LAA 250. The ability of the coiled element 5, 105, 205 to pull the occluder disk 2, 102, 202 toward the orifice 299 of the LAA 250 also allows the occlusion device 1, 102, 202 to effectively seal the orifice 299 of the LAA 250 and thereby substantially or completely prevent blood from exiting the LAA.

The first anchoring element 6, 106, 206 connects to the coiled element 5, 105, 205 and may comprise one or more wires. The wire(s) may form a wire mesh, such as a self-expanding wire mesh. The wire may be made from any type of suitable shape memory material that will cause the wire to form a preferred relaxed state configuration when introduced into the LAA. The material is selected for its biocompatibility, including its anti-thrombogenic capacity, shape-recovery capabilities and superelasticity. The wire(s) may comprise a metal or a metal alloy. The metal or metal alloy may be, for example, a memory alloy. A memory alloy may comprise nickel, titanium or any other suitable material. For example, the memory alloy may be Nitinol®, which is a nickel-titanium alloy, Elgiloy®, titanium, stainless steel, other suitable material or combinations thereof. It is easier to manufacture the first anchoring element 6, 106, 206 when the first anchoring element 6, 106, 206 is only made of one wire because, for example, welding of multiple wires comprising the first anchoring element is unnecessary. Such welding may fail resulting in failure of a portion of or the entire occlusion device, which may lead to severe complications. Such complications may include embolization of a part or of all of the occlusion device and/or may include failure of the occlusion device to occlude all of the LAA.

The first anchoring element 6, 106, 206 includes scalloped edges 96, 196, 296 that are configured to anchor the occlusion device 1, 100, 200 to inner walls of the LAA and to reduce or eliminate the risk of penetration or perforation of the walls of the LAA. As a result, the first anchoring element 6, 106, 206 does not distend the LAA and does not have any barbs, hooks, or loops of wire that might cause the first anchoring element 6, 106, 206 to have a sharp end, where sharp ends are prone to perforate the inner walls of the LAA. Scalloped edges may substantially resemble or resemble a wave formation, such as a sinusoidal shape.

The nondistending nature of the occlusion device and the lack of any sharp ends/edges are beneficial. For example, the first anchoring element 6, 106, 206 may avoid complications observed in conventional occlusion devices, which generally have straight wire, protruding wire barbs that can penetrate the LAA wall, thereby causing perforation of the muscle of the LAA wall. The incidence of perforation or pericardial effusion rate is greater than 0% for these conventional devices because the devices can penetrate the walls of the LAA. Examples of such devices include the Amplatzer cardiac plug and the Watchman device. The effusion rate and overall complication rate are 3.5% and 7%, respectively, for the Amplatzer cardiac plug (*Catheter Cardiovasc Interv.* 2011 Apr. 1; 77(5):700-6. doi: 10.1002/ccd.22764. Epub 2011 Mar. 8). The effusion rate and overall complication rate are between 2.2-5.0% and 3.7-10.0%, respectively, for the Watchman device (*Circulation.* 2011 Feb 1; 123(4):417-24. Epub 2011 Jan. 17). Unlike these conventional devices, the first anchoring element 6, 106, 206 has an effusion rate of 0%. This effusion rate of 0% was found for the first and second canine occlusion study that is discussed later in the present application under the heading "Non-Limited Working Example." Additionally, in stark contrast to conventional occlusion devices, the occlusion devices described herein can effectively overcome other challenges and complications faced by existing devices. For example, the occlusion devices described herein can prevent erosion, arrhythmia, life-threatening bleeding or compression of the circumflex coronary artery. The aforementioned complications and challenges may result in myocardial infraction and/or death The scalloped edges 96, 196, 296 are preferable to smoothed edges, such as shown in FIGS. 19A-21B, because the scalloped edges 96, 196, 296 more securely anchor the first anchoring element 96, 196, 296 to the LAA without substantial or any risk of the first anchoring element 96, 196, 296 unintentionally detaching from the LAA so that the occlusion device 1, 100, 200 migrates from the LAA.

The first anchoring element or anchor component 6, 106, 206 may also be concave shaped, thereby further assisting to prevent unintentional migration of the occlusion device 1, 100, 200 from the LAA. The concave shape of the first anchoring element 6, 106, 206 may allow the scalloped edges 96, 196, 296 to exert an outward distending force against the wall of the LAA so that the first anchoring element 6, 106, 206 actively engages the interior walls of the LAA. Such engagement prevents the occlusion device from migrating out of the LAA because the scalloped edges 96, 196, 296 of the first anchoring element 6, 106, 206 catch the interior walls of the LAA due to the outward force exerted by the occlusion device. Preferably, the widest diameter of the first anchoring element 6, 106, 206, where the first anchoring element 6, 106, 206 is intended to engage the walls of the LAA, is wider than the diameter of the interior walls of the LAA so that the first anchoring element 6, 106, 206 can engage and exert an outward distending force against the wall of the LAA.

As shown in FIGS. 6-10, the occlusion device 100, 200 may also include a self-centering element 103, 203 that connects to the occluder disk 102, 202 and the middle element 197, 297 and that is configured to center the occlusion device 100, 200 within the orifice of the left atrial appendage 250. The self-centering element 103, 203 may be integrally connected with the occluder disk 102, 202 or may be coupled to the occluder disk 102, 202. The self-centering element 103, 203 comprises one or more wire and the wire(s) may form a wire mesh. When the self-centering element 103, 203 is integrally connected with the occluder disk 102, 202, the self-centering element 103, 203 and the occluder disk 102, 202 may comprise the same wire(s). When the self-centering element 103, 203 and the occluder disk 2, 102, 202 are not integrally connected, the self-centering element 103, 203 and occluder disk 102, 202 each comprise separate wire(s).

The wire(s) of the self-centering element 103, 203 is preferably made of the same material as the wire(s) of the occluder disk 102, 202. For example, the self-centering element 103, 203 may be made from any type of suitable shape memory material that will cause the wire(s) to form a preferred relaxed state configuration when introduced into the LAA. The material is selected for its biocompatibility, including its anti-thrombogenic capacity, shape-recovery capabilities and superelasticity. The wire(s) may comprise a metal or a metal alloy. The metal or metal alloy may be, for example, a memory alloy. A memory alloy may comprise nickel, titanium or any other suitable material. For example, the memory alloy may be Nitinol®, which is a nickel-titanium alloy, Elgiloy®, titanium, stainless steel, other suitable material or combinations thereof. Alternatively, the self-centering element 103, 203 may be made of a different material than the wire(s) of the occluder disk 102, 202.

It is easier to manufacture the self-centering element 103, 203 when the self-centering element 103, 203 is only made of one wire because, for example, welding of multiple wires comprising the self-centering element is unnecessary. Such welding may fail resulting in failure of a portion of or the entire occlusion device, which may lead to severe complications. Such complications may include embolization of a part or of all of the occlusion device and/or may include failure of the occlusion device to occlude all of the LAA.

Figure 8:
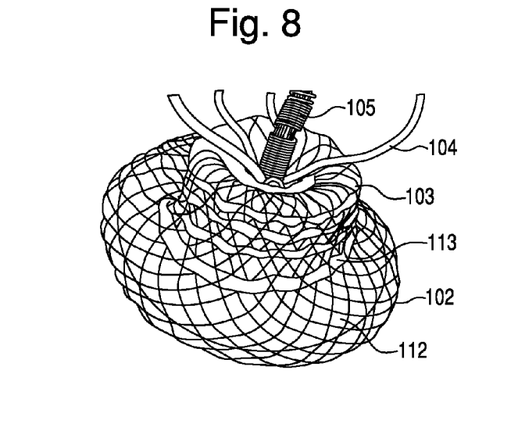
FIG. 8 is a top perspective view of a portion of the occlusion device of FIG. 6.

The self-centering element 103, 203 may include a second fabric material 113, 213. The second fabric material 113, 213 may be woven around the wire(s) that comprise the self-centering element 103, 203 (FIG. 8). The second fabric material 113, 213 may also be woven around a portion of the occluder disk 102, 202 (FIG. 8) that is adjacent to and/or abuts the self-centering element 103, 203, such that the second fabric material 113, 213 is woven around the wire(s) of the occluder disk 102, 202. Alternatively or in addition to being woven around the wire(s), the second fabric material may be any suitable shape that fits within or on the surface of the occluder disk 102, 202. For example, the second fabric material may be or additionally include a sheet, a plurality of sheets, a membrane or a random shape. The sheet, plurality of sheets, membrane or random shape may extend along an inside surface of the occluder disk 102, 202 in a flagged manner such that the length and width of the second fabric material may extend along the inside surface of the occluder disk 102, 202 for any length and width sufficient to ensure that the second fabric material can assist in ensuring that the orifice of the LAA will be substantially or completely eclipsed by the second fabric material 12, 112, 212.

The second fabric material 113, 213 may be any suitable material that promotes and/or facilitates tissue growth so that tissue of the subject can grow in and around the self-centering element. For example, the second fabric material 113, 213 may comprise polyester fibers, such as Dacron®. Alternatively, the second fabric material 113, 213 may be made of a biodegradable and/or biocompatible material such as expanded polytetrafluoroethylene (ePTFE), Teflon®, felt, Gortex® (a PTFE material), silicone urethane, metal fibers, other polymers, such as polypropylene or combinations thereof. The second fabric material 113, 213 may be impermeable to fluid, such as blood or body fluid. Like the first fabric material, the second fabric material 113, 213 may also substantially or completely prevent blood flow in and out of the LAA through the self-centering element 103, 203. While the second fabric material and the first fabric material generally are separate structures, they may form an integral structure.

The self-centering element 103, 203 may be conical, cylindrical. circular, tapered (FIGS. 19A-19B) or irregular (FIGS. 20A-20B) shaped. FIGS. 6-9 show an example where the self-centering element 103, 203 is cylindrical shaped. The conical, cylindrical or circular shape of the self-centering element 103, 203 enables outer walls of the self-centering element 103, 203 to abut or be flush with the inner walls of the LAA when the occlusion device 100, 200 is delivered into the LAA. The alignment of the outer walls of the self-centering element 103, 203 with the inner walls of the LAA self-center the occlusion device 100, 200, thereby allowing for easy positioning of the occlusion device 100, 200 within the LAA and preventing the occluder disk from falling or prolapsing into the LAA. The easy positioning of the occlusion device and prevention of the occluder disk from falling or prolapsing is an improvement over conventional occlusion devices. Conventional occlusion devices may include an orifice occluder that covers the orifice of the LAA, such as disclosed in U.S. application Ser. No. 11/271,751, but comparison of such conventional occlusion devices to the occlusion devices of the present application, reveals that devices with orifice occluders allow for the occlusion device to tip or be angled within the occlusion device. Such tipping or angling allows blood to exit the LAA because the orifice of the LAA is not completely or substantially occluded. The comparison also showed that the occlusion device of the present application, which includes a self-centering element, did not tip or angle, thereby allowing substantial or complete occlusion of the orifice of the LAA. The possible shape (circular, cylindrical, elliptical, tapered, irregular) of the self-centering element may be chosen based on the geometry of the LAA in which the occlusion device is intended to be deployed. For example, a cylindrical shaped self-centering element may be advantageous in a shorter LAA.

Figure 1:
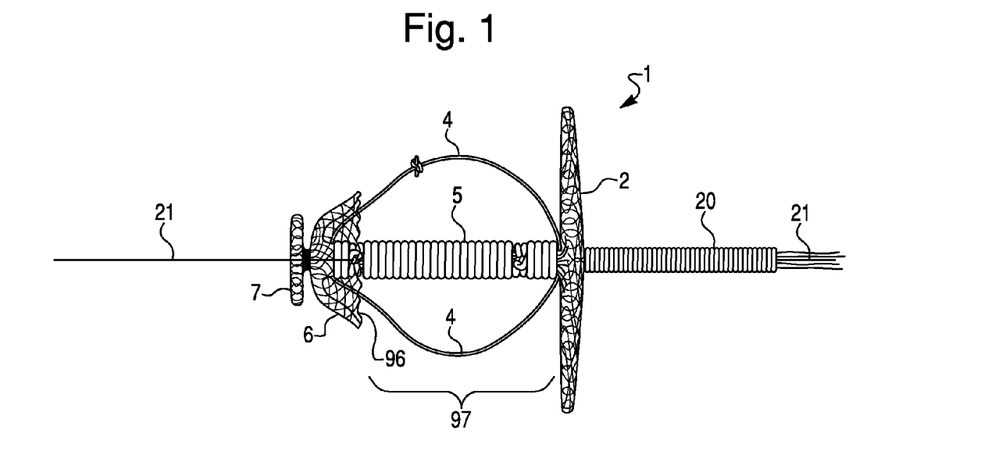
FIG. 1 is a side view of a LAA occlusion device and a catheter.
Figure 2:
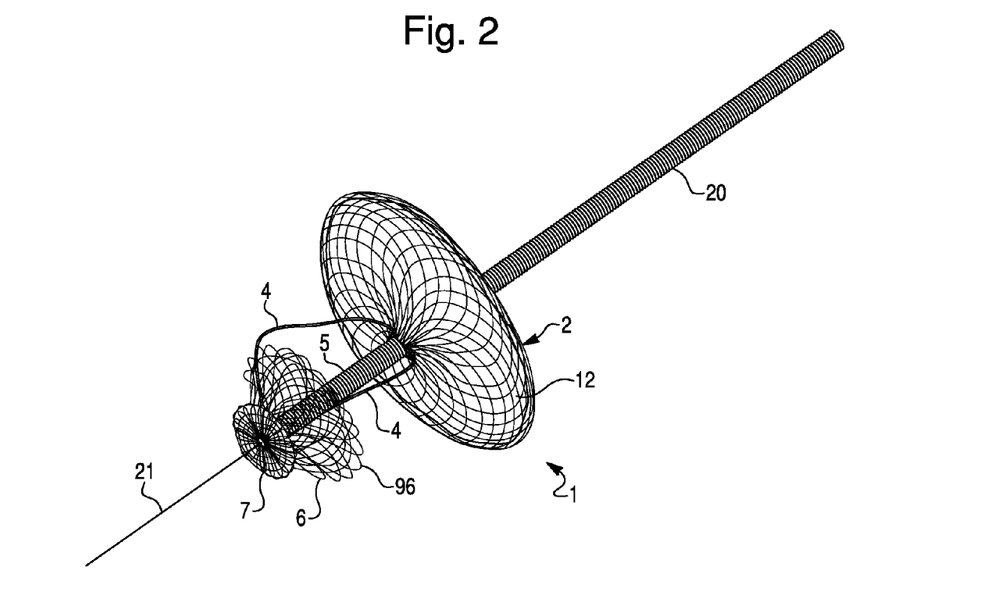
FIG. 2 is a side perspective view of the occlusion device and catheter of FIG. 1.
Figure 3:
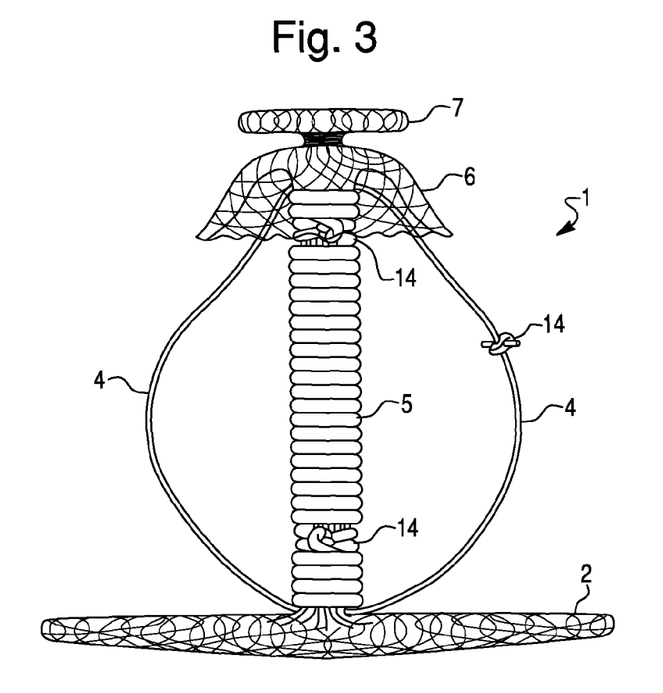
FIG. 3 is a side view of the occlusion device of FIG. 1.
Figure 4:
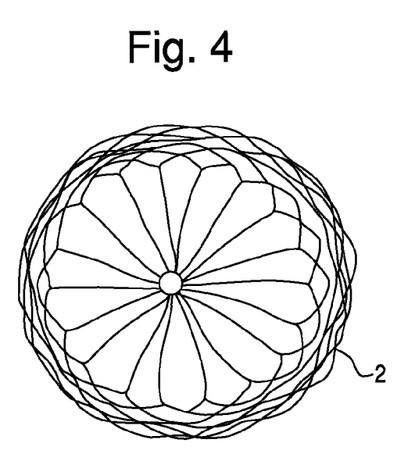
FIG. 4 is a bottom view of the occlusion device of FIG. 3 showing the occluder disk.
Figure 5:
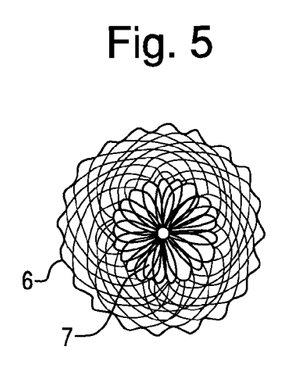
FIG. 5 is a top view of the occlusion device of FIG. 4 showing first and second anchoring elements.

Beside the coiled element, the middle portion 97, 197, 297 may also include at least two stabilizing strings 4, 104, 204 that comprise a substantially or completely non-elastic material such that the stabilizing strings 4, 104, 204 prevent elongation of the coiled element 5, 105, 205 past a predetermined length. Because the stabilizing strings, 4, 104, 204 or retention springs prevent elongation of the coiled element 5, 105,

205 past a predetermined length, the retention springs 4, 104, 204 prevent the coiled element from being overstretched during loading or retrieving of the occlusion device within the LAA. As shown in FIGS. 1-3, the middle portion 97 may include two stabilizing strings. As shown in FIGS. 6 and 8-10, the middle portion 197, 297 may include four stabilizing strings. The more stabilizing strings, the harder it is for the coiled element 5, 105, 205 to extend past the predetermined length in any given direction. The predetermined length is the length of or substantially the length of the stabilizing strings 4, 104, 204. Consequently, the stabilizing strings 4, 104, 204 may serve to prevent the occlusion device 1, 100, 200 from overstretching and may, therefore, be referred to as "stretch stabilizing strings."

The stabilizing strings 4, 104, 204 may comprise any suitable material. For example, the strings may comprise (or be made from) the material of the wire, Gortex®, silk, 05 to 0.12 Nitinol, any fabric thread monofilament or polyfilament, polyester thread mono or polyfilament, nylon thread/wire, metal such as steel, biodegradable material or combinations thereof.

The stabilizing strings 4, 104, 204 may be part of the coiled element 5, 105, 205 or may be a separate component. The stabilizing strings 4, 104, 204 may extend from the first anchoring element 6, 106, 206 to the self-centering element 103, 203 (FIGS. 6, 8-9) or the occluder disk 2 (FIG. 2). Alternatively, the stabilizing strings 4, 104, 204 may extend from the first anchoring element 6, 106, 206 to the self-centering element 103, 203 and the occluder disk 2.

Figure 6:
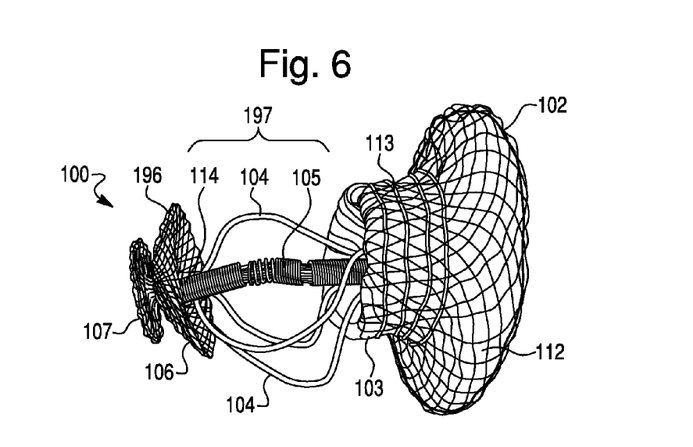
FIG. 6 is a side view of a LAA occlusion device.
Figure 7:
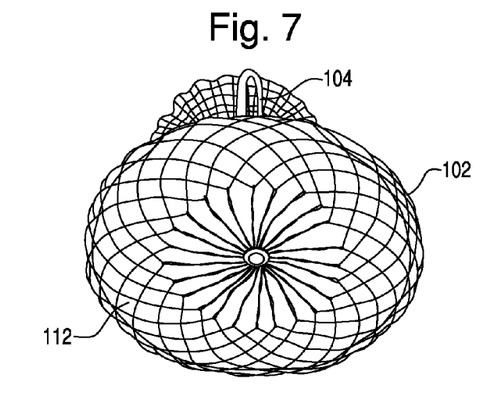
FIG. 7 is a bottom perspective view of the occlusion device of FIG. 6.
Figure 9:
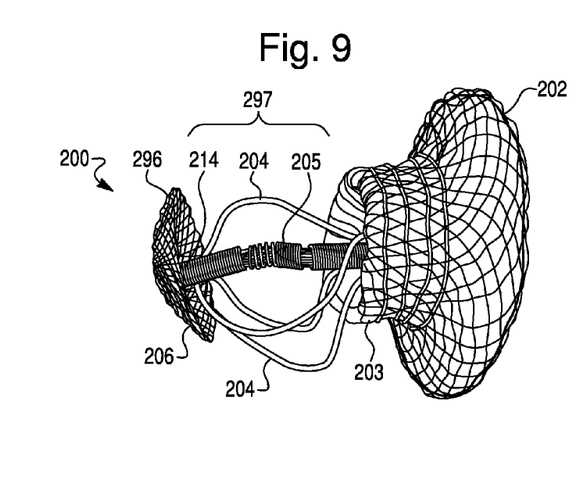
FIG. 9 is a side view of a LAA occlusion device.

The stabilizing strings 4, 104, 204 may couple to the first anchoring element 106, 116, 216 and at least one of the self-centering element 103, 203 and the occluder disk 102, 202. As shown in FIGS. 3, 6 and 9, the stabilizing strings 4, 104, 204 may be attached to the first anchoring element 106, 116, 216 and at least one of the self-centering element 103, 203 and the occluder disk 102, 202 by fastening the stabilizing strings 4, 104, 204 to the first anchoring element 106, 116, 216 and at least one of the self-centering element 103, 203 and the occluder disk 102, 202. The stabilizing strings 4, 104, 204 may be fastened by tying knots 14, 114, 214. Additionally, the stabilizing strings 4, 104, 204 may extend through the coiled element 5, 105, 205. When the stabilizing strings 4, 104, 204 extend through the coiled element 5, 105, 205, the stabilizing strings 4, 104, 204 may also fasten to the coiled element (FIGS. 1, 3, 6, 9) to couple the stabilizing strings 4, 104, 204 to the first anchoring element 106, 116, 216 and at least one of the self-centering element 103, 203 and the occluder disk 102, 202.

As shown in FIGS. 1-6, the occlusion device 1, 100 may also include one (FIGS. 1-6) or more second anchoring elements 7, 107. As shown in FIGS. 1-6, the second anchoring element 7, 107 may connect to the first anchoring element 6, 106. The second anchoring element 7, 107 may be integrally connected with the first anchoring element 6, 106 or may be coupled to the first anchoring element 6, 106. The second anchoring element 7, 107 comprises one or more wire and the wire(s) may form a wire mesh. When the second anchoring element 7, 107 is integrally connected with the first anchoring element 6, 106, the second anchoring element 7, 107 and the first anchoring element 6, 106 may comprise the same wire(s).

The wire(s) of the second anchoring element 7, 107 is preferably the same material as the wire(s) of the first anchoring element 7, 107. For example, the second anchoring element 7, 107 may be made from any type of suitable shape memory material that will cause the wire(s) to form a preferred relaxed state configuration when introduced into the LAA. The material is selected for its biocompatibility, including its anti-thrombogenic capacity, shape-recovery capabilities and superelasticity. The wire(s) may comprise a metal or a metal alloy. The metal or metal alloy may be, for example, a memory alloy. A memory alloy may comprise nickel, titanium or any other suitable material. For example, the memory alloy may be Nitinol®, which is a nickel-titanium alloy, Elgiloy®, titanium, stainless steel, other suitable material or combinations thereof. It is easier to manufacture the second anchoring element 7, 107 when the second anchoring element 7, 107 is only made of one wire because, for example, welding of multiple wires comprising the second anchoring element is unnecessary. Such welding may fail resulting in failure of a portion of or the entire occlusion device, which may lead to severe complications. Such complications may include embolization of a part or of all of the occlusion device and/or may include failure of the occlusion device to occlude all of the LAA. Alternatively, the wire(s) of the second anchoring element 7, 107 may be a different material from the wire(s) of the first anchoring element 7, 107.

The occluder disk 2, 102, 202, self-centering element 103, 203 and first anchoring element 6, 106, 206 may each comprise one or more wires. The occluder disk, the self-centering element and the first anchoring element may comprise a single wire or the occluder disk and the self-centering element may comprise a single wire and the first anchoring element may comprise a single wire.

Figure 22:
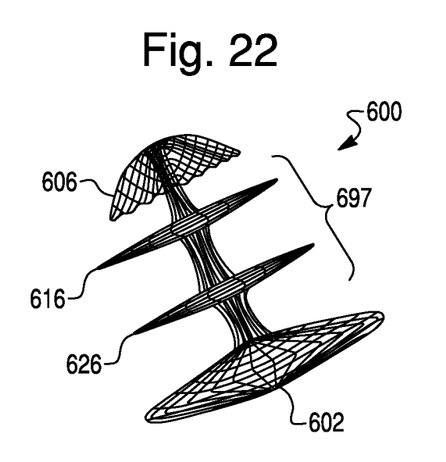
FIG. 22 is a side perspective view of a LAA occlusion device.

While the middle portion 97, 197, 297 of FIGS. 1-10 is shown including a coiled element 5, 105, 205 having a coiled shape, the middle portion may not have a coiled shape. As shown in FIG. 22, the middle portion 697 may be a wire mesh that includes a plurality of second anchoring elements, 616, 626 and cylinder portions extending between the second anchoring elements 616, 626. One or more of the second anchoring elements 616, 626 may assist the first anchoring element 606 in anchoring the occluding device 600 to inner walls of the LAA. Alternately, one or more of the second anchoring elements 616, 626 may assist the occluder disk 602 in substantially preventing or completely preventing blood flow from exiting the LAA.

Figure 11:
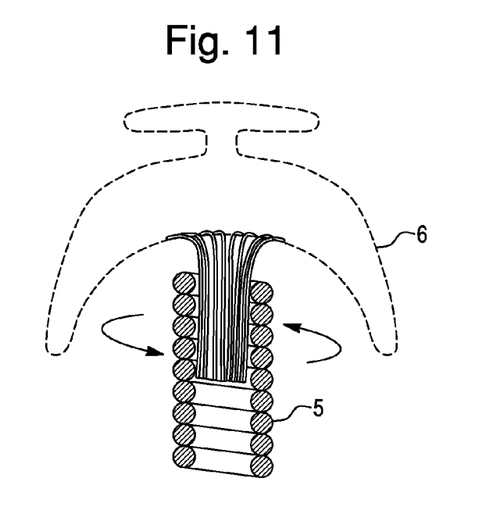
FIG. 11 is a side view of a portion of a first and second anchoring element of an occlusion device being attached to a middle portion.
Figure 12:
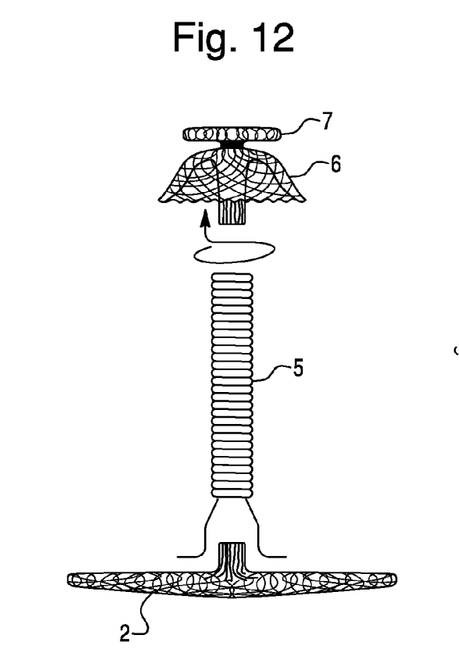
FIG. 12 is a side view of a first and second anchoring element and occluder disk being attached to a middle portion.
Figure 13:
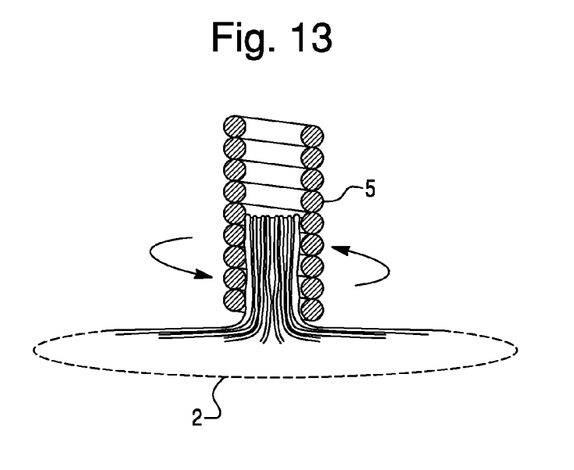
FIG. 13 is a side view of an occluder disk being attached to a middle portion.

FIGS. 11-13 illustrate how various elements of the occlusion device 1 may be coupled together. As shown in FIG. 11, the wire(s) of the first anchoring element 6 may extend through a portion of the inner diameter of the coiled element 5 and, as shown in FIG. 13, the wire(s) of the occluder disk 2 may also extend through a portion of the inner diameter of the coiled element 5. The stabilizing strings may be used to couple the first anchoring element 6 to the coiled element 5 and the occluder disk 2 to the coiled element 5. Although not shown, when the occlusion device includes a self-centering element, the self-centering element may extend through a portion of the inner diameter of the coiled element 5 or the self-centering element and the occluder disk may extend through a portion of the inner diameter of the coiled element 5.

As shown in FIGS. 1-2 a wire 21 may extend through the occlusion device 1 and/or a catheter 20 where the catheter 20 may assist in deploying the occlusion device 1 inside of the LAA and the wire 21 may assist in delivering the occlusion device 1 to the LAA. The catheter 20 may also be referred to as a control catheter. The catheter 20 may house the wire 21 or wires. The catheter 20 is attached to the control catheter 20 by the wire 21 or wires. The catheter 20 may allow pushing and pulling of the occlusion device 1 in and out of a delivery sheath. When the catheter 20 is pushed, the occlusion device 1 expands. When the catheter 20 is pulled, the occlusion device 1 collapses. The delivery sheath has a larger diameter than the catheter 20 and is generally a hollow tube that is positioned within the LAA when the occlusion device is delivered to the LAA.

Once delivered to the LAA, the occlusion device expands into the shape shown in FIGS. 1-3, 6-10 and 14A-22 such that, as shown in FIGS. 10, 19A, 20A and 21A, the first anchoring device 206, 306, 406, 506 anchors the occlusion device 200, 300, 400, 500 to inner walls of the LAA 250, the occluder disk 202, 302, 402, 502 aids in substantially or completely preventing blood from exiting the LAA 250 and the self-centering element 203 centers the occlusion device 200 within the LAA 250. When the occlusion device expands, the flexible nature of the occlusion device allows the occlusion device to bend to conform to the natural shape of the LAA. As shown in FIGS. 10, 19A, 20A and 21A, the occlusion device 200, 300, 400, 500 may bend at an angle of 45 to 90 degrees to conform to the natural shape of the LAA. The coiled element 205 may allow the occlusion device 200 to bend at such an angle (FIG. 10).

Figure 14A:
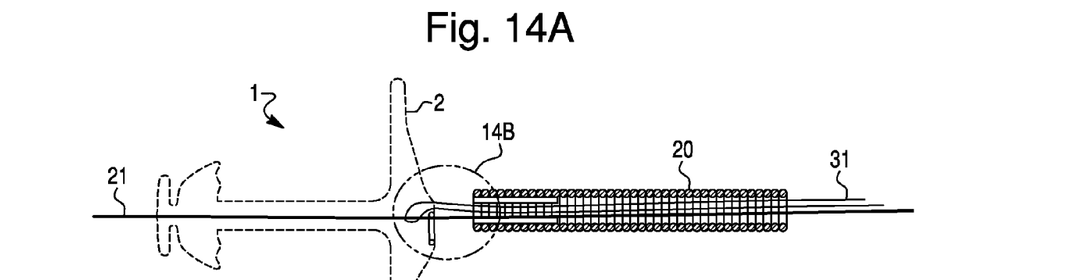
FIG. 14A is a side view of a LAA occlusion device before being released from a catheter.
Figure 14B:
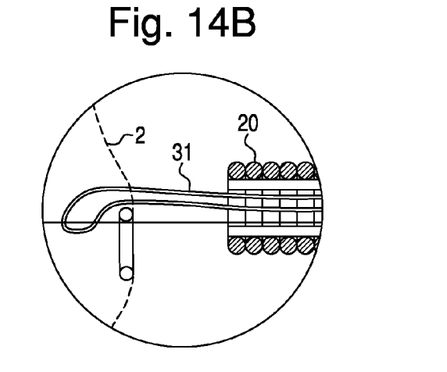
FIG. 14B is a detailed view of section 14B of FIG. 14A.

FIGS. 14A-18 further illustrate wire(s) and catheter(s) help deliver an occlusion device 1 to the LAA where FIGS. 14A-18 show the occlusion device before being released from a catheter by an attachment/release mechanism. As shown in FIGS. 14A-14B, a catheter 20 includes a wire 21 that extends through the occlusion device 1. The catheter 20 also includes a looped or released wire 31 that hooks onto the occluder disk 2 of the occlusion device 1 and loops around the wire 21. When a force is exerted on the released wire 31, such as by someone pulling the released wire 31, the occlusion device 1 does not release into the LAA, but when a force is exerted on the wire 21, such as by someone pulling the wire 21 through the occlusion device 1, the released wire 31 becomes free or unassociated with the wire(s) of the occluder disc 2 and the occlusion device 1 is no longer attached to the control catheter 20. Consequently, the occlusion device 1 is released into the LAA. FIG. 14B shows a detailed view of the detachment zone or detachment mechanism of the attachment/release mechanism before the wire 21 is pulled through the loop 31 (i.e. before the released wire 31 is released from the wire 21). The mechanisms of releasing the occlusion device shown in FIGS. 15A-18 operate similarly to the mechanism of releasing the occlusion device shown in FIGS. 14A-14B.

Figure 15A:
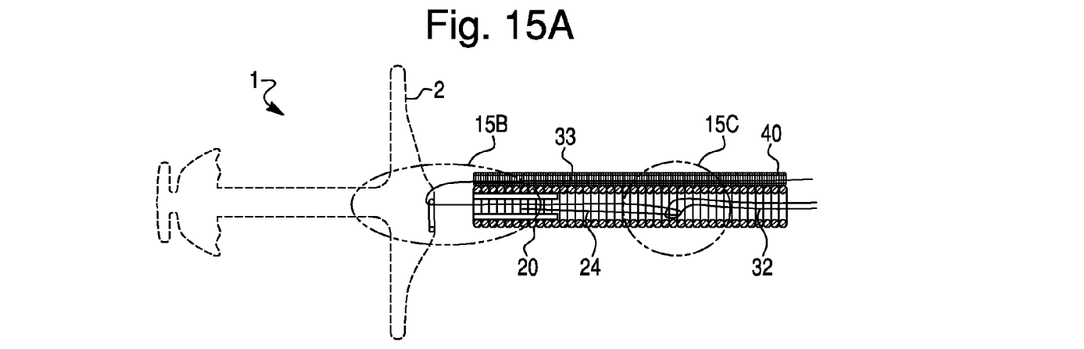
FIG. 15A is a side view of a LAA occlusion device before being released from catheters.
Figure 15B:
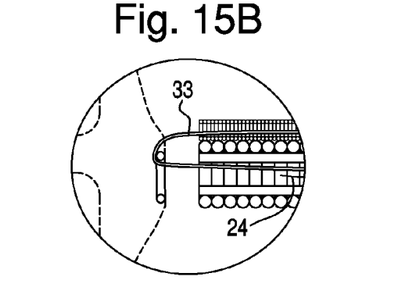
FIG. 15B is a detailed view of section 15B of FIG. 15A.
Figure 15C:
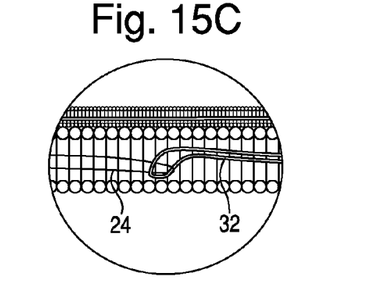
FIG. 15C is a detailed view of section 15C of FIG. 15A.
Figure 16:
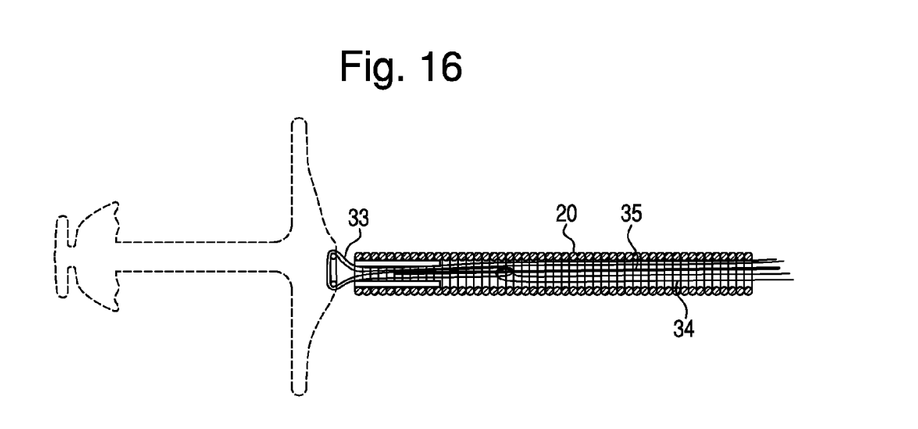
FIG. 16 is a side view of a LAA occlusion device before being released from a catheter.
Figure 17:
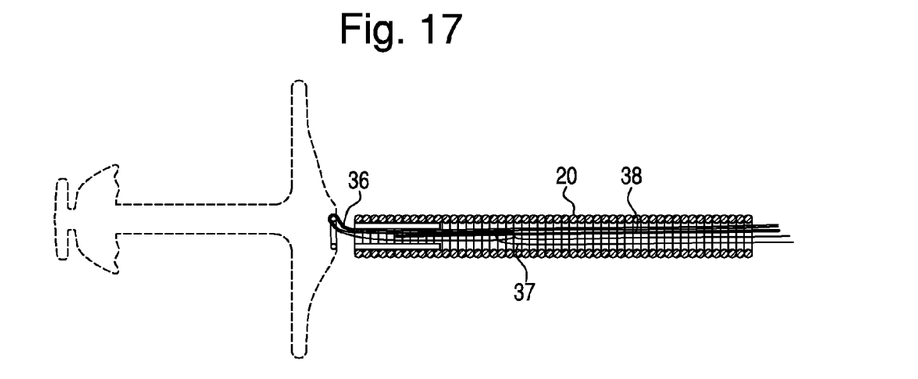
FIG. 17 is a side view of a LAA occlusion device before being released from a catheter.
Figure 18:
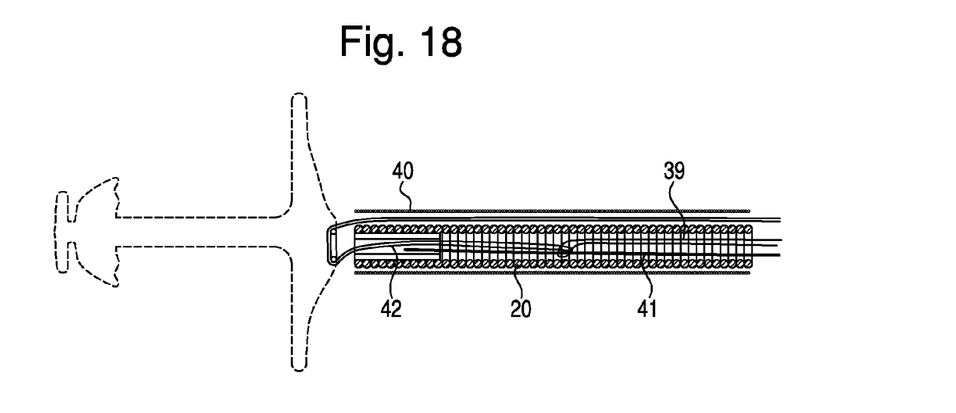
FIG. 18 is a side view of a LAA occlusion device before being released from a catheter.
Figure 19A:
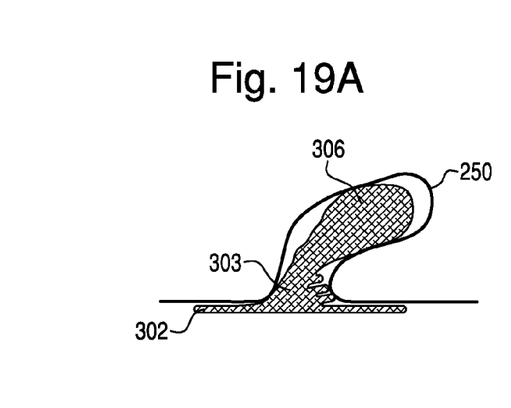
FIG. 19A is a side view of a LAA occlusion device after being delivered into the LAA.
Figure 19B:
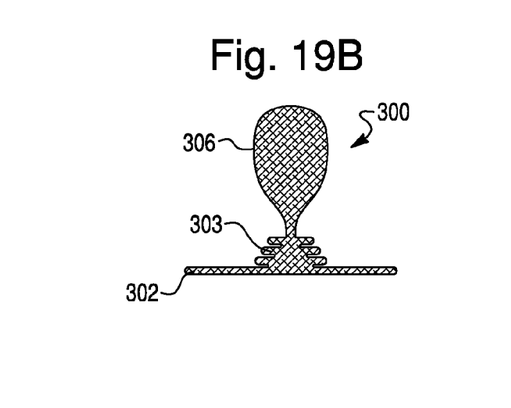
FIG. 19B is a side view of the occlusion device of FIG. 19A.
Figure 20A:
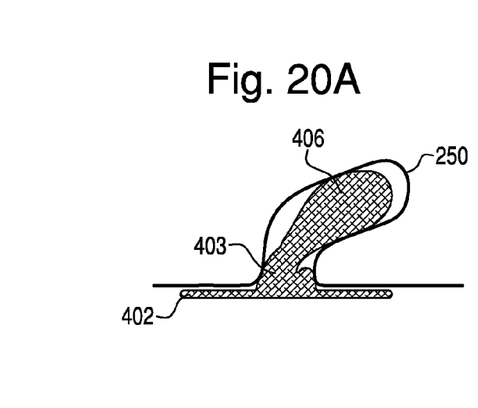
FIG. 20A is a side view of a LAA occlusion device after being delivered into the LAA.
Figure 20B:
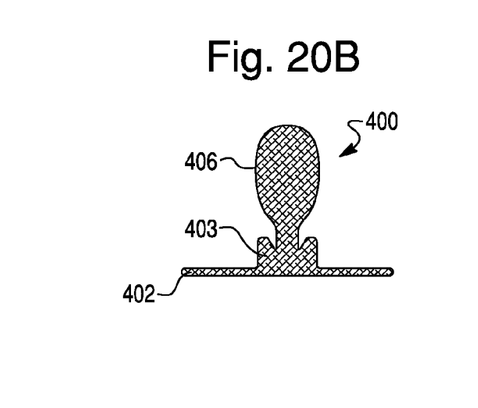
FIG. 20B is a side view of the occlusion device of FIG. 20A.
Figure 21A:
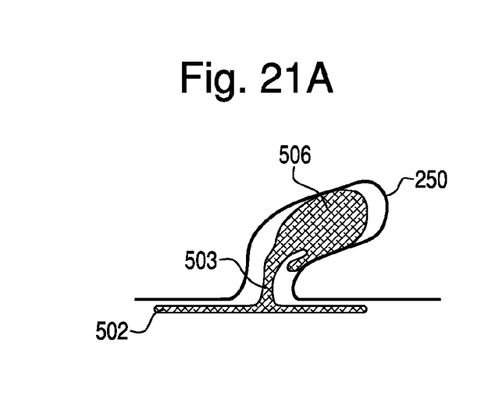
FIG. 21A is a side view of a LAA occlusion device after being delivered into the LAA.
Figure 21B:
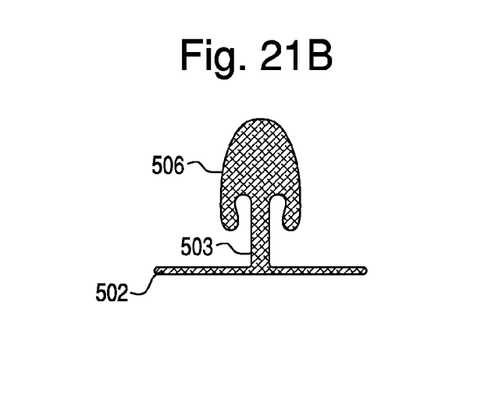
FIG. 21B is a side view of the occlusion device of FIG. 21A.

As shown in FIGS. 15A-18, the number of catheters and wires and/or the location of the wires may vary. As shown in FIGS. 15A-15C, a delivery catheter 20 and a second catheter 40 may be used. A wire 24 and a released wire 32 or looped wire may extend through the delivery catheter 20. A looped wire 33 may extend through the delivery catheter 20 and the second catheter 40. The looped wire 33 may hook onto the occluder disk and may loop around the released wire 32. The released wire 32 may loop around the wire 24. The delivery catheter 20 and the second catheter 40 may reside within a delivery sheath (not shown) to facilitate deliver of the occlusion device to the LAA. When the delivery catheter 20 and the second catheter 40 reside in a delivery sheath, the occlusion device resides within the delivery sheath and abuts the catheters 20, 40 before deployment of the occlusion device into the LAA. Similar to FIGS. 15A-15C, FIG. 18 also includes a delivery catheter and a second catheter. Unlike FIGS. 15A-15C, the looped wire 42 of FIG. 18 hooks onto two locations of the occluder disk as opposed to one location. Similar to FIGS. 14A-14B, FIGS. 16-17 include a delivery catheter. Unlike FIGS. 14A-14B, the looped wire 33 of FIG. 16 hooks onto two locations of the occluder disk as opposed to one location, while FIG. 17 includes two looped wires.

The respective components, and thus the occlusion device, may have various shapes, depending on the application. For example, the occluder disk can have a larger average diameter than the first anchoring element, and vice versa. The middle portion may be perpendicular to the occluder disk and/or first anchoring element, or it can be attached to the occluder disk and the first anchoring element at a non-90 degree angle. The occlusion device may have any shape, such as an ellipsoid, spherical or cylindrical shape. Alternately, as shown in FIGS. 19A-21B, the occlusion device may not include a middle portion.

Any of the elements of the occlusion device, including the strings and the fabric material, may have anti-coagulant coating or a coating to promote endothelial cell growth in order to aid in the prevention of clot formation around the sheet. The anti-coagulant coating may include heparin, an albumin-binding coating, phosphorylcholine, poly-D, L-lactic acid, prostaglandin, dextran sulfate, or other peptide suitable for coagulation prevention. The coating to promote endothelial cell growth may include pyrolytic carbon, a cryoprecipitate-based coating, autologous fibrin meshwork, elastin-based polypeptides, fibronectin, collagen IV, a fibronectin-collagen IV combination, extracellular matrix proteins and peptides, plasma polymerized coating or other suitable material to encourage growth of endothelial cells on the sheet.

The presently described occlusion devices have advantages over the existing devices particularly with respect to improvement in safety. For example, the occlusion devices may minimize stretching or distending of the LAA, thereby avoiding complications that might arise therefrom.

An additional advantage of the presently described occlusion devices is its small size, and the improvement in safety arising therefrom. When the occlusion device is being inserted into a subject's body, the insertion may take place via an 8 French sheath (or tube). One French is about 0.33 mm. This is in stark contrast to the existing devices, which generally are delivered through 12-14 French sheaths, because of their larger size. Thus, the presently described occlusion devices are about 33-42% smaller than the existing devices. The overall diameter or the largest diameter of the occlusion devices among the different components of the occlusion devices may be less than or equal to about 3 mm, such as less than about 2.5 mm, such as less than about 2 mm. The smaller size of the present occlusion devices may provide the benefit of reducing risk of damage to the femoral vein, where the sheath generally enters, or damage to the atrial septum, left atrium, or LAA, where the sheath generally passes. Additionally, a larger sheath would generally need a larger hole in the atrial septum to be created for insertion; the larger the sheath, the greater the potential is for introducing air into the blood stream—this can cause heart attack, stroke, and death of the subject.

Non-Limiting Working Example

Two canine LAA occlusion studies were conducted using the protocol reported in 2002 by Nakai et al, in which 25 dogs were implanted. All results of the studies were presented to peers at international cardiology conferences. The Nakai study was conducted with a grossly different device from that of the LAA devices disclosed in the present application. Canines were tested because the LAA of canines is nearly identical to the LAA of humans. Canines have been used in a surgical model for occluding the LAA (14 canines that underwent thoracotomy for placement of an external LAA "clip" were described by Fumoto et al in 2008).

The aim of the first canine LAA occlusion study was to assess safety, feasiblity, and efficacy of implantation of a LAA occlusion device disclosed in the present application that does not include a self-centering element. The aim of the second canine LAA occlusion study was to assess safety, feasiblity, and efficacy of implantation of a LAA occlusion device disclosed in the present application that includes a self-centering element.

In the first study, three sets of 7 dogs for a total of 21 animals were chosen. The main purpose for having three sets of seven dogs was to document both on gross inspection as well as microscopic (histologic) evaluation and consistency in the degree of endothelialization over time (e.g. one, three and sixth months post implamantation of the occlusion device within the dogs). In humans, endothelialization of an intracardiac device is typically complete by 6 months. The results of the first canine LAA occlusion study revealed that a low profiled delivery release of the occlusion device was feasible though a 8-9 Fr sheath and that the coiled element allowed for adjustable length of the occlusion device to accommodate varying LAA sizes. The results also showed that the first and second anchoring elements did not perforate the walls of the LAA and that the occluder disk conformed to the wall of the left atrium, thereby promoting endothelialization and occlusion of the LAA orifice. Additionally, the results showed that the occlusion device did not stretch, distend or perforate the LAA, thereby reducing the risk of bleeding from perforation and potentially life threatening circumflex coronary artery compression. Results showed that the development of embolization from the LAA was rare. Additionally, light and electron microscopy results confirmed normal endothelial cellular growth over the occluder disk.

In the second study, 18 dogs were tested. 18 dogs were tested to document both on gross inspection as well as microscopic (histologic) evaluation and consistency in the degree of endothelialization over time (e.g. one, three and sixth months post implamantation of the occlusion device within the dogs). In humans, endothelialization of an intracardiac device is typically complete by 6 months. The results of the second canine LAA occlusion study revealed that a low profiled delivery release of the occlusion device was feasible though a 8-9 Fr sheath and that the coiled element allowed for adjustable length of the occlusion device to accommodate varying LAA sizes. The self-centering element and coiled element allowed for successful positioning the occlusion device within the LAA. The self-centering element also ensured that the occlusion device did not tip or angle within the orifice of the LAA, thereby allowing the occlusion device to substantially or completely prevent blood from entering or exiting the LAA. The results also showed that the first and second anchoring elements did not perforate the walls of the LAA. It was found that the use of only a first anchoring element and not a first and second anchoring element resulted in not perforating the walls of the LAA and achieving successful anchoring. Results showed that the occluder disk conformed to the wall of the left atrium, thereby promoting endothelialization and no gaps between the occlusion device and the left atrial wall and LAA orifice. Additionally, the results showed that the occlusion device did not stretch, distend or perforate the LAA, thereby reducing the risk of bleeding from for perforation and potentially life threatening circumflex coronary artery compression. There were no instances of bleeding or pericardial effusion. Results showed that the development of embolization from the LAA was rare. Additionally, results showed that acute occlusion rates were high and light and electron microscopy results confirmed normal endothelial cellular growth over the occluder disk.

All publications, patents, and patent applications cited in this Specification are hereby incorporated by reference in their entirety.

As utilized herein, the articles "a" and "an" are used to refer to one or to more than one (i.e. to at least one) of the grammatical object of the article. By way of example, "a polymer resin" means one polymer resin or more than one polymer resin. Any ranges cited herein are inclusive. As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature. For the purpose of this disclosure, the term "between" does not require direct connect between surfaces.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the LAA occlusion device or components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. A left atrial appendage occlusion device comprising:
   (i) an occluder disk, configured to substantially prevent blood from at least one of entering and exiting the left atrial appendage;
   (ii) a middle portion that includes a coiled element, wherein the coiled element connects to the occluder disk, has a substantially constant cross section and allows for at least one of variable length, variable orientation, and varied angles of the occlusion device; and
   (iii) a first anchoring element that connects to the coiled element and includes scalloped edges that are configured to anchor the occlusion device to inner walls of the left atrial appendage and reduce the risk of one of penetration and perforation of walls of the left atrial appendage.

2. The device of claim 1, wherein the occluder disk includes a first fabric material impermeable to fluid.

3. The device of claim 2, wherein the first fabric material comprises at least one of polyester fabric, polytetrafluoroethylene (ePTFE), Teflon, felt, Gortex, silicone urethane, metal fibers and polypropylene.

4. The device of claim 1, further comprising a self-centering element that connects to the occluder disk and the middle portion and that is configured to center the occlusion device within the orifice of the left atrial appendage.

5. The device of claim 4, wherein the self-centering element and the occluder disk are one of coupled together and integrally formed.

6. The device of claim 4, wherein the self-centering element includes a second fabric material impermeable to fluid that is configured to facilitate tissue growth over the occlusion device.

7. The device of claim 6, wherein the second fabric material comprises at least one of polyester fabric, polytetrafluoroethylene (ePTFE), Teflon, felt, Gortex, silicone urethane, metal fibers and polypropylene.

8. The device of claim 4, wherein the self-centering element is one of conical, cylindrical, tapered and circular.

9. The device of claim 4, wherein the middle portion further includes at least two stabilizing strings that comprise a substantially non-elastic material such that the stabilizing strings prevent elongation of the coiled element past a predetermined length and prevent overstretching of the coiled element during loading or retrieval of the occlusion device from the left atrial appendage.

10. The device of claim 9, wherein the predetermined length is the length of the stabilizing strings.

11. The device of claim 9, wherein there are two stabilizing strings.

12. The device of claim 9, wherein there are four stabilizing strings.

13. The device of claim 9, wherein the stabilizing strings comprise at least one of PTFE, silk, a memory alloy, a fabric thread monofilament or polyfilament, a polyester thread mono or poylfilament, a Nylon, steel and biodegradable material.

14. The device of claim 9, wherein the stabilizing strings extend from the first anchoring element to at least one of the self-centering element and the occluder disk.

15. The device of claim 9, wherein the stabilizing strings couple to the first anchoring element and at least one of the self-centering element and the occluder disk.

16. The device of claim 1, further comprising one or more second anchoring elements connected to at least one of the first anchoring element and the middle portion.

17. The device of claim 4, wherein the occluder disk, the self-centering element and the first anchoring element each comprise a single wire.

18. The device of claim 4, wherein the occluder disk and the self-centering element comprise a single wire and the first anchoring element comprises a single wire.

* * * * *